United States Patent [19]

Kallis

[11] 4,281,062
[45] Jul. 28, 1981

[54] TEST FOR THE IDENTIFICATION OF GLUCOSE AND FOR THE DETERMINATION OF GLUCOSE

[75] Inventor: Karl-Heinz Kallis, Sebnitz, German Democratic Rep.

[73] Assignee: Veb Arzneimittelwerk Dresden, Radebeul, German Democratic Rep.

[21] Appl. No.: 60,168

[22] Filed: Jul. 23, 1979

[30] Foreign Application Priority Data

Jul. 25, 1978 [DD] German Democratic Rep. ... 206900

[51] Int. Cl.³ ............................................ C12Q 1/54
[52] U.S. Cl. ..................................... 435/14; 435/28; 435/296; 422/56
[58] Field of Search .................. 435/14, 28, 175, 288, 435/296, 300, 25; 422/56

[56] References Cited

U.S. PATENT DOCUMENTS

| 3,359,180 | 12/1967 | Evans et al. | 435/14 |
| 3,552,925 | 1/1971 | Fetter | 435/14 X |
| 3,811,840 | 5/1974 | Bauer et al. | 435/14 X |
| 3,964,871 | 6/1976 | Hochstrasser | 435/28 X |
| 4,046,514 | 9/1977 | Johnston et al. | 435/14 X |

*Primary Examiner*—Thomas G. Wyse
*Attorney, Agent, or Firm*—Michael J. Striker

[57] ABSTRACT

Glucose identification and determination test. A test strip contains a metering zone, a reaction zone with glucose oxidase, and an indicator zone having at least one indicator signal zone of peroxidase and indicator applied in the form of stripes alternating with untreated intermediate spaces. The metering zone may be impregnated with a colorant, oxidizing, precipitating or buffering agent. The glucose oxidase is applied in an acid solution below the isoelectric point to prevent substrate inhibition by means of test fluid diffusion and may be in the form of an immobilized suspension. Together with a flow-inducing agent, the test strip allows a reaction not influenced by the time elapsed after sampling. Intermediate zones located between the reaction zone and the metering zone and/or the identification zone may be prepared with buffering substances. The test strip may be located within a capillary tube of 1-3 mm diameter and 40-120 length made of glass or plastic.

13 Claims, 4 Drawing Figures

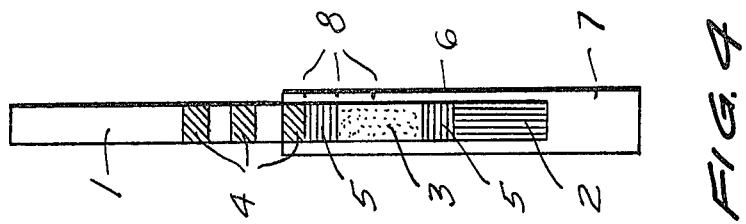
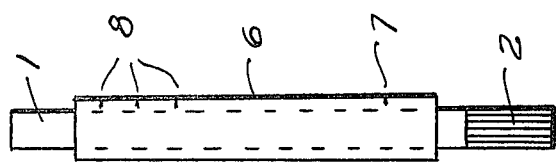
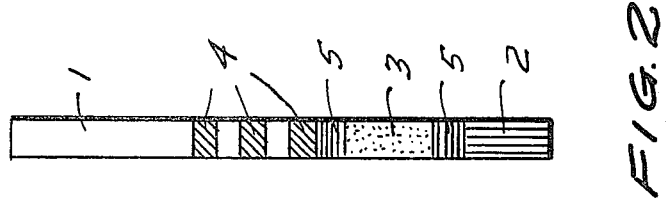

TEST FOR THE IDENTIFICATION OF GLUCOSE AND FOR THE DETERMINATION OF GLUCOSE

The invention relates to a test for the identification of glucose and for the determination of glucose. The enzymatic reaction of glucose with the enzyme glucose oxidase, and demonstration with suitable indicators in the presence of the auxiliary enzyme peroxidase or of similar-acting substances is known, as is the application of this principle for strip tests.

Color reactions will always occur herein, and are evaluated visually or by photometry. With lower concentrations of glucose, the color reactions can be distinguished by their difference, but with rising quantities of glucose within the pathologically important range, classification becomes more difficult, and, with the test strips as described hitherto, obtaining of unequivocal results is no longer possible. This can be ascribed to the fact that in the tests as used hitherto, the components required for the reaction are applied within one zone and that the ensuing reactions will occur parallel to each other. The importance of the micro-environment and of diffusion will thus increase with rising quantities of substrate.

The method already described for demonstrating glucose with separately applied indicator zones for glucose oxidase and peroxidase, is suitable only for a qualitative proof and has the same disadvantages, since the enzyme glucose-oxidase will diffuse, together with the test fluid and the substrate, or the product of its reaction respectively, into the peroxidase zone. The pH-optimum for both enzymes is different, so that no optimal conditions exist for the conjointly applied components.

A further disadvantage results from the fact that, with an increased time of reaction, the colorants as formed will continue to oxidize and mixed colors will originate, so that an extended reaction will not bring about an improvement in the method of determination. These disadvantages were rectified in the methods described hitherto by adding gelatine or polymers, and by the selection of suitable buffers. Visual evaluation has also been facilitated by the addition of yellow or red colorants.

The evaluation of all tests as described, is made by means of a color table or with the aid of special measuring devices, wherein the latter requires a reference measurement to be made. Due to the reasons as noted afore, evaluations must be made within a prescribed reaction time and read-off time which must be adhered to, in order to use the color table or the measuring instrument.

These disadvantages of poor differentiating, difficult correlation with the color table, and the need to maintain the reaction time and the time for read-off, are furthermore affected by the drop in enzyme activity and by nuisance factors originating from the test material.

Thus, the simultaneous application of test strips or foils for the determination of glucose, in the urine as well as in the serum or blood, is not possible, since with the principle of reaction as known the albumin content and the colorant content require a special preparation of the tests. For this purpose, the reaction zone is made hydrophobic or is lined with a semi-permeable layer.

A special form of determination has been developed to identify the glucose remaining in the urine, and to distinguish an absolutely glucose-free urine from urines with physiological amounts up to 30 mg/100 ml (Journal of the American Medical Association April 15, 1968, vol. 204, pp. 206 to 208). For this, the carrier-material paper is pretreated with 2-diethylaminoethanol.

The problem of determing glucose quantities below 40 mg/100 ml, in serum or blood, present as diagnostic problem in pediatry, cannot be solved with the test strips as hitherto described, since no indication will yet occur within this range.

Series determinations cannot be made by an individual laboratory technician, since the requirement of simultaneously maintaining the reaction and read-off times will limit the number of tests. Unskilled persons such as age-related diabetics may have difficulties in the visual reaction under the prescribed conditions and using color tables as furnished, and this, will limit a wide application of the tests for self testing.

It is the objective of the invention, to develop a test allowing quantified drawing-off of the test fluid, allowing immediate or later glucose determination individually or in series without the need for exact maintenance of a reaction and read-off time, the test being so prepared that glucose may be determined in the urine as well as in serum or blood.

It is the task of the invention to create a test for glucose determination, whereby the quantity of the test fluid for the reaction and the reaction time of the former with the ferment glucose oxidase is controlled in such a manner that either the color gradation is improved, or that a color comparison is no longer needed, and whereby the quantitative determination also of higher glucose concentrations is possible, and which will enable, respectively, the detection of the remaining glucose, or the determination of glucose quantities below 40 mg/100 ml in urine, serum or blood. The task enumerated above is solved as per invention by having a test strip consist of a minimum of three zones: a metering zone, a reaction zone and an identification zone.

The metering zone serves for absorbing and measuring a certain amount of the test fluid without a reaction having to occur. This zone may additionally be provided with means of marking and thus be distinguished by coloring. It may furthermore contain means for oxidizing, buffering, or precipitation, so that, for instance, albumin, haemoglobin, or vitamin C, will be bonded.

Above this metering zone, a reaction zone with affixed glucose oxidase is arranged. Surprisingly, it has been found that glucose oxidase can be immobilized to a sufficient extent, without essentially limiting its activity, if applied in an acid solution below the isoelectric point. This is, considering the expenditure, an economically advantageous method since in this way, no retreatment losses will occur in the sample. A glucose oxidase initially immobilized by a known method can, of course, be applied as suspension.

An identification zone is arranged after the reaction zone. The auxiliary enzyme peroxidase and an indicator is applied in one zone, or several strips in the form of signal zones, are applied, the zones being interstices. If several peroxidase indicator zones are applied in the form of signal zones. The interstices may contain a color-retaining fixative. A safety space either delimited by color and/or saturated with reagents for buffering or marking purposes may be arranged between the metering and the reaction zones. A neutral buffer zone, unprepared or prepared with buffering substances, can be inserted between the reaction and identification zones.

The spacing between the metering zone and the reaction zone on one hand, and the reaction and identification zones on the other may be held different.

A capillary tube made of glass or plastic serves to retain the test strip. The capillary tube is provided at its lower end with a colored mark, up to which a predetermined quantity of flow-inducing agent is accommodated. The capillary tube has a length of 40 to 120 mm, preferably of 60 mm. It is made with a uniform internal diameter of 1 to 3 mm, preferably 2.5 mm. In its upper section, the capillary tube is provided with a colored graduation. This graduation serves to indicate the quantity of glucose in the test fluid. Since the concentration of glucose is equivalent to the length of the colored identification zone, a quantitative determination for the glucose can be obtained by reading from the divisions of the graduation.

If the test strip as per invention is used with capillary tubes, it is not necessary to maintain a predetermined reaction time. To implement the glucose identification, the metering zone of the test strip projecting out of the capillary tube, is to be immersed. The test strip can be pushed back into the capillary tube immediately, or after the metering zone has absorbed the test fluid. The identifying reaction is initiated by absorbing a flow-inducing agent up to the lower mark of the capillary tube, and wetting of the metering zone.

Sample drawing and reaction proceed independently of each other. The course of the reaction on the test strip can be initiated, in conjunction with the capillary tube at any desired moment and in series, by the absorption of a flow-inducing agent. Using a capillary tube will allow precise and adequate dosage, also by unskilled personnel or lay persons.

If the test strip as per invention is to be used without a capillary tube, it will be appropriate to arrange the metering, reaction, and identification zones on the strip, without providing intermediate or safety spaces. In this case, the identification of glucose is made by immersing the test strip to the full height of the metering zone and evaluating the length of the identifying indicator on the identification zone. This identification allows at least a semi-quantitative identification of glucose.

The test strip as per invention obviates the need for using a color table. The test is so designed that, on one hand, it will allow identification of the lowest glucose quantities. On the other hand, a substrate inhibition is prevented by the diffusion of the test fluid through the glucose-oxidase reaction zone. By this, it will be possible to distinguish also between higher concentrations.

Example of Realization

The invention is to be explained more closely, using several embodiments.

Shown in the relative drawings:

FIG. 1: a test strip usable without capillary tube

FIG. 2: a test strip with indicator signal zones usable with capillary tubes

FIG. 3: capillary tube with test strip for the absorption of the test fluid

FIG. 4: capillary tube with test strip for the absorption of the flow-inducing agent

EXAMPLE 1

The example describes the semi-quantitative identification of glucose in the urine without a color table and without limiting the reaction or reading times in individual or series determinations, and is shown in FIG. 1.

Filter paper with a weight of 100 $g/m^2$ is used as carrier material. A 0.1% solution of Sudan red in ethanol is prepared and an assessing zone 2 of 5 to 15 mm width is marked at one end of a test strip 1. The width of this zone is to be set corresponding exactly to the widths of the subsequent zones. A width of 10 mm is set in the example.

For the reaction zone 3, separate solutions are prepared of (a) 0.1 glucose benzoic acid in 10 ml ethanol (b) 3,000 U glucose oxidase in 10 ml distilled water, mixed together and applied immediately with a width of 3 to 10 mm, 5 mm in the present instance, above the 10 mm wide zone of Suden red.

For the identification zone 2, separate solutions are prepared of (a) 300 U peroxidase in 10 mm buffer 0.2 mol, pH 7.0, and (b) 100 mg o-tolidine and 10 mg auramine yellow in 10 ml ethanol, mixed together and applied onto the paper above the reaction zone 3. The mixed solution may be applied in stripes of 1 to 2 mm width, for instance in 4 stripes spaced apart, or, as shown, in the form of a wide strip of 10 mm width.

Application of the three solutions for the different zones is suitably effected by the known lining machines. The paper sheets or webs are dried in the known manner thereafter, and cut into strips. Usng it for a test, the portion of the test strip 1 marked for metering, is momentarily submerged into the test fluid, f.i. urine. The absorbed quantity of the fluid will suffice to diffuse, by capillary action, through the glucose-oxidase zone into the peroxidase indicator zone, or zones respectively. A definite amount of glucose is reacted thereby and indicated in the peroxidase indicator zone. The quantity of glucose is indicated by the length of the peroxidase indicator zone, or zones respectively, that become colored thereby. Since the reaction terminates at the end of the diffusion, the coloring, which ensues depending upon the glucose content, will remain constant, also after the fluid has evaporated.

The strip may therefore be evaluated at any desired time.

EXAMPLE 2

This example explains the production of a test strip, provided with an indicator-signal zone, to be used, with a capillary tube but without color table and pre-determined read-off time in identifying glucose in urine, for self-testing and also for series identification, as depicted in FIGS. 2 to 4.

A suitable carrier material with good absorption, f.i. filter paper with an area weight of 135 $g/m^2$, simultaneously with the solutions as described in the respective following instances.

Metering zone 2, width 10 mm.

A solution of 0.1 g potassium permanganate and 100 mg Congo red in 100 ml distilled water, is prepared and applied to the lower edge with a width of 10 mm. Reducing substances, such as ascorbic acid which may interfere with the reaction and may possibly be present in the urine, will be reacted within this zone.

Intermediate zone 5, width 5 mm, subsequent to the metering zone 2.

A solution of 1 g nitrilo-3-acetic acid in 100 ml distilled water, is prepared and applied with a width of 5 mm. This zone serves as masking zone.

Reaction zone 3, width 10 mm.

A solution of 0.5 succinic acid in 50 ml distilled water, and a solution of 0.5 glucose oxidase, corresponding to 15,000 U, in 50 ml distilled water are prepared. The two solutions are mixed and the mixture immediately applied with a width of 10 mm over the intermediate zone 5.

Intermediate zone 5, width 5 mm adjacent to the reaction zone 3.

A solution of 1 g sodium acetate in 100 ml water is prepared and applied 5 mm wide. This zone serves as buffer zone.

Identification zone 4

Adjacent to the intermediate zone 5, a total of 5 peroxidase indicator zones, with a respective width of 2 to 3 mm, are applied, with spaces of 2 to 3 mm in-between. For this, a solution of the following composition is used:
 (a) 100 mg peroxidase, corresponding to 600 U, dissolved in 50 ml of a 0.2 mol buffer solution, pH 7,2
 (b) 400 mg o-tolidine and 75 mg Orasol yellow, dissolved in 500 mm ethanol Both solutions are mixed together and immediately applied as afore, above the intermediate zone 5.

Application of the various solutions may be made simultaneously or in succession. The prepared and dried carrier material is cut into narrow tapes about 2 mm wide, and inserted into the capillary tubes 6 made of glass or plastic. The capillary tubes 6 have a mark 7 for the metering of the flow-inducing agent. The capillary tubes 6 are 60 mm long, with an internal diameter of 2.5 to 3 mm. For performing the test, the metering zone 2, dyed red, is pushed out of the capillary tubes 6 and briefly immersed into the test fluid.

By this, a quantified fluid absorption will ensue. Possibly present reducing substances, particularly ascorbic acid, will be oxidized. Reaction of the glucose will, however, not yet take place. Subsequently, the strip is pulled into the capillary tube 6 until the lower edge is about 5 mm above the mark 7 of the capillary tube 6.

Depending upon whether an individual determination or series determinations are to be performed, the glucose determination will ensue immediately, or as desired. For this, the capillary tube 6 is filled up to the mark 7 by immersion into distilled water. Subsequently, the test strip 1 is pushed into the water and stood upright. Capillary action will cause the test fluid to diffuse with the water through the various zones, and the glucose is brought to reaction. Depending upon the glucose content, one or several indicator zones will become colored and can be read-off from the graduation 8.

Assuming that the process of diffusion has been concluded, reading-off and evaluation may be made at any time, as desired, since the coloring will remain constant. Instead of potassium permanganate any other suitable oxidizing or recipitation agent may be added to the metering zone 2, since the marking agent may also be varied in the manner as known. Substances with the effect of peroxidase, as described in literature, may likewise be used for the identification zone 4. Using other known indicator systems instead of o-tolidine for the identification of hydrogen peroxide is also possible.

EXAMPLE 3

Preparation of a test with indicator signal zones for the identification and determination of traces of glucose, in the urine in case of infections of the urinary tract, and in the serum, or blood respectively, of children, without the color table and without predetermined read-off, as depicted in FIGS. 2 to 4.

A filter paper with an area weight of 220 g/m² is used as carrier.

Zone 2.
 1. Zone, width 10 mm, without preparation,
 2. Zone, width 10 mm, impregnated with a solution of 0.05 g peroxidase permanganate in 100 ml water.

Reaction zone 3, width 10 mm

Impregnated width a mixture of the solutions of
 (a) 1 g bezoic acid in 50 ml ethanol,
 (b) 1 g glucose oxidase in 50 ml water, corresponding to 30,000 U.

Identification zone 4, width 10 mm, subsequent to the reaction zone 3. This zone is impregnated with a mixture of the following solutions:
 (a) 200 mg peroxidase corresponding to 600 U dissolved in 50 ml of a 0.2 mol buffer solution, pH 7,2
 (b) 1 g o-tolidine and 50 mg Orasol yellow, dissolved in 50 ml ethanol.

The solutions of different zones are applied immediately or in succession. Strips 2 mm wide and about 7 mm long are cut after drying and pushed into the capillary tube 6. The capillary tubes 6 have an internal diameter of 2,5 to 3 mm. They are so marked that 40 μl of the test fluid can be taken up by them. The test strip which is pulled up for a certain length over the marking 7, the test fluid is taken up, and the test strip 1 inserted. Due to the need to differentiate between very small quantities of glucose and physiologically normal contents, this work is performed only with the test fluid. Evaluation is made using the graduation 8 on the capillary tube 6.

I claim:

1. Test for the identification of glucose and for the determination of glucose, comprising locating, in given instances within a capillary tube marked at both its ends, a test strip which, conjointly with a flow-inducing agent, will allow a reaction not influenced by the time elapsed after sampling, the test strip containing a metering zone, a reaction zone with glucose oxidase applied in an acid solution below the isoelectric point and affixed to it to prevent a substrate inhibition by means of the diffusion of the test fluid taking place within it, and an indicator zone having at least one indicator signal zone of peroxidase and indicator applied in the form of stripes and alternating with untreated intermediate spaces.

2. Test as per claim 1, characterized by the metering zone being impregnated with a colorant, oxidizing, precipitating or buffering agent.

3. Test as per claim 2, characterized by the intermediate space being located within the identification zone containing a fixing agent for the colorant.

4. Test as per claim 1, characterized by the reaction zone containing as a suspension glucose oxidase which has been immobilized.

5. Test as per claim 1, characterized by an intermediate zone located between the metering zone and the reaction zone.

6. Test as per claim 5, wherein said intermediate zone is different in color from said metering zone and said reaction zone.

7. Test as per claim 5, wherein said intermediate zone is saturated with reagents for buffering and masking purposes.

8. Test as per claim 1, characterized by locating between the reaction zone and the identification zone an intermediate zone.

9. Test as per claim 8, wherein said intermediate zone further comprises buffering substances.

10. Test as per claims 5, 6, 7 or 8, characterized by the intermediate zones being of different widths.

11. Test as per claim 1, characterized by the capillary tube having an internal diameter of 1–3 mm and a length of 40–120 mm and being of glass or a plastic of glass-like transparency.

12. Test as per claim 11, wherein said internal diameter is 2.5 mm.

13. Test as per claim 11, wherein said length is 60 mm.

* * * * *